US006375959B1

(12) United States Patent
Mallo et al.

(10) Patent No.: US 6,375,959 B1
(45) Date of Patent: Apr. 23, 2002

(54) THICKENING HOMOPOLYMER, PREPARATION PROCESS AND COSMETIC APPLICATIONS

(75) Inventors: Paul Mallo, Chatou; Guy Tabacchi, Castres, both of (FR)

(73) Assignee: Societe d'Exploitation de Produits pour les Industries Chimiques Seppic, Paris Cedex (FR)

( * ) Notice: Subject to any disclaimer, the term of this patent is extended or adjusted under 35 U.S.C. 154(b) by 0 days.

(21) Appl. No.: 09/250,292

(22) Filed: Feb. 17, 1999

(30) Foreign Application Priority Data

Feb. 17, 1998 (FR) .......................................... 98 01 918

(51) Int. Cl.$^7$ ............................ A61K 6/00; A61K 7/00; A61K 7/06; A61K 7/11
(52) U.S. Cl. ................... 424/401; 424/70.1; 424/70.11; 424/70.17; 424/70.16; 514/880; 514/881; 514/846; 514/937
(58) Field of Search ................. 424/401, 70.1, 424/70.11, 70.17, 70.16; 514/880, 881, 846, 937

(56) References Cited

U.S. PATENT DOCUMENTS 5,185,395 A  *  2/1993  Robinson et al. ........... 524/457
5,458,881 A  * 10/1995  Berger et al. ............... 424/401

FOREIGN PATENT DOCUMENTS

| EP | 0 186 361  |   | 9/1990 |
| EP | 0 503 853  |   | 9/1992 |
| EP | 50 503 853 | * | 9/1992 |
| EP | 0 642 781  |   | 9/1995 |
| EP | 0 815 846  |   | 1/1998 |

* cited by examiner

*Primary Examiner*—Thurman K. Page
*Assistant Examiner*—Todd D Ware
(74) *Attorney, Agent, or Firm*—Young & Thompson

(57) ABSTRACT

Process for the preparation of a composition in the form of an inverted latex, comprising an oil phase, an aqueous phase, at least one emulsifier of water-in-oil (W/O) type, at least one emulsifier of oil-in-water (O/W) type, from 20% to 70% by weight, and preferably from 25% to 45% by weight, of a branched or crosslinked anionic polyelectrolyte based on a monomer possessing a strongly acidic function, characterized in that a) an aqueous solution containing the monomers and the optional additives and adjusted beforehand to a pH below 4 is emulsified in an oil phase in the presence of one or more emulsifiers of water-in-oil type, b) the polymerization reaction is initiated by introducing a free-radical initiator into the emulsion formed in a), after which the reaction is left to proceed, c) when the polymerization reaction is complete, one or more emulsifiers of oil-in-water type are introduced at a temperature below 50° C.

6 Claims, No Drawings

THICKENING HOMOPOLYMER, PREPARATION PROCESS AND COSMETIC APPLICATIONS

The present application relates to thickening water-in-oil lattices, to a process for their preparation and to their application as thickeners and/or emulsifiers for skincare products and haircare products or for the manufacture of cosmetic, dermo-pharmaceutical or pharmaceutical preparations.

Various thickeners exist and are already used for these purposes. Natural products such as guar gum or corn starch are known in particular, the drawbacks of which are those inherent to natural products, such as price fluctuations, supply difficulties and random quality.

Synthetic polymers in powder form, mainly polyacrylic acids, are also widely used but have the drawback of requiring neutralization when they are used, since they only develop their viscosity from a pH >6.5 and they are often difficult to dissolve.

Synthetic thickening polymers in the form of an inverted latex, that is to say one in which the continuous phase is an oil, are also known. These latices dissolve extremely quickly; the polymers contained in these inverted lattices are usually acrylamide/alkali metal acrylate copolymers or acrylamide/sodium 2-acrylamido-2-methylpropane-sulphonate copolymers; they are already neutralized and when they are dissolved in water, for example to a concentration of 1%, it is observed that the pH is generally above 6.

However, acrylamide/sodium acrylate copolymers do not develop any appreciable thickening properties when the pH is lowered below 6; on the other hand, the acrylamide/sodium 2-acrylamido-2-methylpropane-sulphonate copolymers described in EP 0,503,853 retain an appreciable thickening capacity even at pH 4.

However, such copolymers have monoacrylamide contents which, although extremely low, could result in making them impossible to use in cosmetics in the near future, following changes in the European legislation on hazardous substances.

The Applicant has thus been concerned with the synthesis and development of polymers that thicken, even at acidic pH, in the form of an inverted latex, without using monoacrylamide.

The subject of the invention is a process for the preparation of a composition comprising an oil phase, an aqueous phase, at least one emulsifier of water-in-oil (W/O) type, at least one emulsifier of oil-in-water (O/W) type, characterized in that the said composition is an inverted latex comprising from 20% to 70% by weight, and preferably from 25% to 45% by weight, of a branched or crosslinked anionic polyelectrolyte based on a monomer possessing a strongly acidic function, characterized in that:

a) an aqueous solution containing the monomers and the optional additives is emulsified in an oil phase in the presence of one or more emulsifiers of water-in-oil type, b) the polymerization reaction is initiated by introducing a free-radical initiator into the emulsion formed in a), after which the reaction is left to proceed, c) when the polymerization reaction is complete, one or more emulsifiers of oil-in-water type are introduced at a temperature below 50° C.

The expression "emulsifier of the water-in-oil type" is understood to denote emulsifiers having an HLB value that is low enough to give water-in-oil emulsions, such as the surfactant polymers sold under the name Hypermer™ or such as sorbitan extracts, for instance sorbitan monooleate sold by the company SEPPIC under the tradename Montane 80™, or sorbitan isostearate sold by SEPPIC under the name Montane 70™.

The expression "emulsifier of the oil-in-water type" is understood to denote emulsifiers having an HLB value that is high enough to give oil-in-water emulsions, such as ethoxylated sorbitan esters, for instance sorbitan oleate ethoxylated with 20 mol of ethylene oxide, castor oil ethoxylated with 40 mol of ethylene oxide, sorbitan laurate ethoxylated with 20 mol of ethylene oxide or lauryl alcohol ethoxylated with 7 mol of ethylene oxide.

The term branched polymer is understood to denote a non-linear polymer which has pendant chains so as to obtain, when this polymer is dissolved in water, a high degree of entangling leading to very high low-gradient viscosities.

The term crosslinked polymer is understood to denote a non-linear polymer in the form of a three-dimensional network which is insoluble in water but swellable in water and thus leading to the production of a chemical gel.

The composition prepared by the process according to the invention can contain crosslinked units and/or branched units.

The subject of the invention is, in particular, a process as defined above, characterized in that the polymerization of its precursor monomers is carried out at a pH below 4, and more particularly below or equal to 3.5.

The strongly acidic function of the monomer containing it is, in particular, a sulphonic acid function or a phosphonic acid function, which are partially or totally salified, and the said monomer is preferably chosen from 2-methyl-2-[(1-oxo-2-propenyl)amino]-1-propanesulphonic acid which is partially or totally salified in the form of the sodium salt or the ammonium salt.

The subject of the invention is, more particularly, a process as defined above, characterized in that the anionic polyelectrolyte is crosslinked and/or branched with a diethylenic or polyethylenic compound in molar proportion, expressed relative to the monomers used, of from 0.005% to 1% and preferably from 0.01% to 0.1%, and preferably that for which the crosslinking agent and/or the branching agent is chosen from ethylene glycol methacrylate, sodium diallyloxyacetate, diethylene glycol diacrylate, diallylurea, trimethylolpropane triacrylate or methylenebisacrylamide.

The latex according to the invention generally contains from 2.5% to 15% by weight, and preferably from 4% to 9% by weight, of emulsifiers, among which from 20% to 50%, in particular from 25% to 40%, of the total weight of the emulsifiers present are of the water-in-oil (W/O) type and in which from 80% to 50%, in particular from 75% to 60%, of the total weight of the emulsifiers are of the oil-in-water (O/W) type. Such latices also form the subject of the present invention.

According to a specific aspect, the composition as defined above is characterized in that the oil phase represents from 15% to 40%, preferably from 20% to 25%, of its total weight.

This oil phase either consists of a commercial mineral oil containing saturated hydrocarbons such as paraffins, isoparaffins or cycloparaffins, having, at room temperature, a density of between 0.7 and 0.9 and a boiling point above 180° C., such as, for example, Exxol™ D 100 S or Marcol™ 52 sold by Exxon Chemical, isohexadecane or isododecane sold by Bayer, or consists of a plant oil or a synthetic oil or of a mixture of several of these oils.

According to a preferred aspect of the present invention, the oil phase consists of Marcol™ 52 or of isohexadecane;

isohexadecane, which is identified in Chemical Abstracts by the number RN=93685-80-4, is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9). It is marketed in France by the company Bayer. Marcol™ 52 is a commercial oil corresponding to the definition of liquid petroleum jellies in the French Codex. This is a white mineral oil in accordance with the FDA Regulations 21 CFR 172.878 and CFR 178.3620 (a) and it is listed in the USA Pharmacopoeia, US XXIII (1995) and in the European Pharmacopoeia (1993).

The latices contain between 20% and 50% water. The latices according to the invention can also contain various additives such as complexing agents, transfer agents or chain-limiting agents.

According to another aspect of the present invention, its subject is a process for preparing the composition as defined above, characterized in that:

a) an aqueous solution containing the monomers and the optional additives is emulsified in an oil phase in the presence of one or more emulsifiers of water-in-oil type,
 b) the polymerization reaction is initiated by introducing a free-radical initiator into the emulsion formed in a), after which the reaction is left to proceed,
 c) when the polymerization reaction is complete, one or more emulsifiers of oil-in-water type are introduced at a temperature below 50° C.

According to a variant of this process, the reaction medium obtained after step b) is concentrated by distillation before step c) is carried out.

According to a preferred variant of the process as defined above, the polymerization reaction is initiated by a redox couple, which may be of organic or inorganic nature, such as the cumene hydroperoxide/sodium metabisulphite couple or the cumene hydroperoxide/thionyl chloride ($SOCl_2$) couple, at a temperature below or equal to 10° C., and is then carried out either in a virtually adiabatic manner up to a temperature above or equal to 40° C., and more particularly above or equal to 50° C., or by controlling the temperature profile. According to another variant of the process as defined above, the polymerization reaction is carried out at constant temperature. In this case, it is advantageous to use azobis(iso-butyronitrile) (AIBN) between 40° C. and 45° C.

According to another preferred embodiment of the process, the starting aqueous solution is adjusted to a pH below or equal to 3.5.

The subject of the invention is also the use of the composition as defined above for preparing a cosmetic, dermo-pharmaceutical or pharmaceutical topical composition.

A topical composition according to the invention, intended to be applied to the skin or mucous membranes of humans or animals can consist of a topical emulsion comprising at least one aqueous phase and at least one oil phase. This topical emulsion can be of the oil-in-water type. More particularly, this topical emulsion can consist of a fluid emulsion, such as a fluid gel or milk. The oil phase of the topical emulsion can consist of a mixture of one or more oils.

A topical composition according to the invention can be intended for cosmetic use or can be used to prepare a medical product intended for the treatment of mucous and skin diseases. In the latter case, the topical composition then contains an active principle which can consist, for example, of an anti-inflammatory agent, a muscle relaxant, an anti-fungal agent or an antibacterial agent.

When the topical composition is used as a cosmetic composition intended to be applied to the skin or mucous membranes, it may or may not contain an active principle, for example a moisturizer, a tanning agent, a sunscreen, an anti-wrinkle agent, a slimming agent, an anti-radical agent, an antiacne agent or an antifungal agent.

A topical composition according to the invention usually contains between 0.1% and 10% by weight of the thickener defined above. The pH of the topical composition is preferably above or equal to 5, more preferably between 6 and 12.

The topical composition can also contain compounds conventionally included in compositions of this type, for example fragrances, preserving agents, dyes, emollients or surfactants.

According to yet another aspect, the invention relates to the use of the novel thickener mentioned above, in accordance with the invention, to thicken and emulsify a topical composition comprising at least one aqueous phase.

The composition according to the invention is an advantageous substitute for those sold under the name Sepigel™ 305 or Sepigel™ 501 by the Applicant, since it also has good compatibility with the other excipients used for the preparation of formulations such as milks, lotions, creams, soaps, baths, balms, shampoos or conditioners.

In particular, the composition is compatible with the concentrates described and claimed in the international publications WO 92/06778, WO 95/04592, WO 95/13863, WO 96/37285, WO 98/22207, WO 98/47610 or FR 2,734, 496, and with the surfactants described in WO 93/08204.

The composition is particularly compatible with Montanov® 68, Montanov™ 82, Montanov™ 202 or Sepiperl™ N. It can also be used in emulsions of the type described and claimed in EP 0,629,396 and in cosmetically or physiologically acceptable aqueous dispersions with an organopolysiloxane compound chosen, for example, from those described in WO 93/05762 or in WO 93/21316.

The composition can also be used to form cosmetically or physiologically acceptable gels that are aqueous at acidic pH, such as those described in WO 93/07856; it can also be used in combination with nonionic celluloses in order to form, for example, styling gels, such as those described in EP 0,684,024, or alternatively in combination with fatty acid esters of a sugar, in order to form compositions for treating the hair or the skin, such as those described in EP 0,603,019, or alternatively in shampoos or conditioners as described and claimed in WO 92/21316, or, lastly, in combination with an anionic homopolymer such as Carbopol™ in order to form hair-treatment products, such as those described in DE 195 23596.

The composition according to the invention is also compatible with active principles such as, for example, self-tanning agents, for instance dihydroxyacetone (DHA) or antiacne agents, and it can thus be introduced into self-tanning compositions such as those claimed in EP 0,715, 845, EP 0,604,249, EP 0,576,188 or in WO 93/07902.

The composition is also compatible with N-acylated derivatives of amino acids, which allows it to be used in soothing compositions especially for sensitive skin, such as those described or claimed in WO 92/21318, WO 94/27561, WO 98/09611 or WO 99/00109.

The examples which follow are intended to illustrate the present invention without, however, limiting it thereto.

EXAMPLE 1

1) Preparation of an Inverted Latex

The following are loaded into a beaker, with stirring 200 g of deionized water 138.1 g of aqueous 48% (by weight) sodium hydroxide solution 343.5 g of 2-methyl-2-[(1-oxo-2-propenyl)-amino]-1-propanesulphonic acid 0.18 g of sodium diethylenetriaminepenta-acetate 0.22 g of methylenebisacrylamide The pH of the aqueous phase described above is adjusted to 3.5 and the amount of aqueous phase is made up to 707 g by adding deionized water.

In parallel, an organic phase is prepared by introducing the following ingredients successively into a stirred beaker:

220 g of isohexadecane 22 g of Montane 80 VG (sorbitan oleate sold by SEPPIC)

0.2 g of azobisisobutyronitrile

The aqueous phase is introduced gradually into the organic phase and is then subjected to vigorous mechanical stirring of ultra-turrax™ type sold by IKA.

The emulsion obtained is then transferred into a polymerization reactor. A large amount of nitrogen is bubbled through the emulsion so as to remove the oxygen, and the resulting emulsion is cooled to about 5–6° C.

5 ml of a solution containing 0.42% (by weight) of cumene hydroperoxide in isohexadecane are then introduced.

After a period which is sufficient to obtain good homogenization of the solution, aqueous sodium metabisulphite solution (0.4 g in 100 ml of water) is then introduced at a rate of 0.5 ml/minute. The introduction is carried out over about 60 minutes.

During this introduction, the temperature in the polymerization reactor is allowed to rise to the final polymerization temperature.

The reaction medium is then held at this temperature for about 90 minutes.

The mixture is cooled to a temperature of about 35° C. and 30 g of sorbitan oleate ethoxylated with 20 mol of ethylene oxide are introduced slowly.

The desired emulsion having the viscosities below is obtained:

Viscosity at 25° C. of the latex at 3% in water (Brookfield RVT, No. 6 spindle, speed 5): n=93,800 mPa.s.

2) pH Stability of the Latex

The measurements of the viscosity of gels containing 3% of the inverted latex prepared in the above paragraph at acidic pH, adjusted with a dilute lactic acid solution, show that this latex is stable:

| pH | n |
|---|---|
| 3.04 | 76.800 |
| 4.00 | 94.000 |
| 5.00 | 93.000 |

3) "Break" Effect

Cosmetic formulations are prepared with each of the latices prepared in paragraphs A to C above, these formulations comprising:

0.5%, 1%, 1.5%, 2%, 2.5% or 3% latex

5% Simulsol 165,

20% Lanol 1688, 0.5% Sepicide HB water qs 100%.

It is observed that the feel sensation of these emulsions is very specific at and above 1% polymer in the solution and this difference increases as the concentration increases; it is a very fresh feel sensation at the start, which melts completely on the skin, this feel sensation not being experienced at all with the latices of the prior art.

EXAMPLE 2

Care Cream

| | |
|---|---|
| Cyclomethicone: | 10% |
| Compound of Example 1: | 0.8% |
| Montanov ™ 68: | 4.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 3

Care Cream

| | |
|---|---|
| Cyclomethicone: | 10% |
| Compound of Example 1: | 0.8% |
| Montanov ™ 68: | 4.5% |
| Perfluoropolymethyl Isopropyl ether: | 0.5% |
| Preserving agent: | 0.65% |
| Lysine: | 0.025% |
| EDTA (disodium salt): | 0.05% |
| Pemulen ™ TR: | 0.2% |
| Glycerol: | 3% |

EXAMPLE 4

Aftershave Balm

| FORMULA | | |
|---|---|---|
| A | Compound of Example 1: | 1.5% |
| | Water: | qs 100% |
| B | Micropearl ™ M 100: | 5.0% |
| | Sepicide ™ CI: | 0.50% |
| | Fragrance: | 0.20% |
| | 95° ethanol: | 10.0% |

Procedure

Add B to A.

EXAMPLE 5

Satin Body Emulsion

| FORMULA | | |
|---|---|---|
| A | Simusol ™ 165: | 5.0% |
| | Lanol ™ 1688: | 8.50% |
| | Karite butter: | 2% |
| | Liquid paraffin: | 6.5% |
| | Lanol ™ 14M: | 3% |
| | Lanol ™ S: | 0.6% |
| B | Water: | 66.2% |
| C | Micropearl ™ M 100: | 5% |
| D | Compound of Example 1: | 3% |
| E | Sepicide ™ CI: | 0.3% |
| | Sepicide ™ HB: | 0.5% |

-continued

| FORMULA | | |
|---|---|---|
| | Monteine ™ CA: | 1% |
| | Fragrance: | 0.20% |
| | Vitamin E acetate: | 0.20% |
| | Sodium pyrrolidinonecarboxylate: | 1% (moisturizer) |

Procedure

Add C to B, emulsify B in A at 70° C. and then add D at 60° C., followed by E at 30° C.

EXAMPLE 6

Body Milk

| FORMULA | | |
|---|---|---|
| A | Simusol ™ 165: | 5.0% |
| | Lanol ™ 1688: | 12.0% |
| | Lanol ™ 14M: | 2.0% |
| | Cetyl alcohol: | 0.3% |
| | Schercemol ™ OP: | 3% |
| B | Water: | qs 100% |
| C | Compound of Example 1: | 0.35% |
| D | Sepicide ™ CI: | 0.2% |
| | Sepicide ™ HB: | 0.5% |
| | Fragrance: | 0.20% |

(Schercemol ™ OP is a non-greasy emollient ester)

Procedure

Emulsify B in A at about 75° C.; add C at about 60° C., followed by D at about 30° C.

EXAMPLE 7

O/W Cream

| FORMULA | | |
|---|---|---|
| A | Simusol ™ 165: | 5.0% |
| | Lanol ™ 1688: | 20.0% |
| | | 1.0% (stabilizing additive) |
| B | Water: | qs 100% |
| C | Compound of Example 1: | 2.50% |
| D | Sepicide ™ CI: | 0.20% |
| | Sepicide ™ HB: | 0.30% |

Procedure

Introduce B into A at about 75° C.; add C at about 60° C., followed by D at 45° C.

EXAMPLE 8

Non-greasy Antisun Gel

| FORMULA | | |
|---|---|---|
| A | Compound of Example 1: | 3.00% |
| | Water: | 30% |
| B | Sepicide ™ CI: | 0.20% |
| | Sepicide ™ HB: | 0.30% |
| | Fragrance: | 0.10% |
| C | Dye: | q.s. |
| | Water: | 30% |

-continued

| FORMULA | | |
|---|---|---|
| D | Micropearl ™ M 100: | 3.00% |
| | Water: | q.s. 100% |
| E | Silicone oil: | 2.0% |
| | Parsol ™ MCX: | 5.00% |

Procedure

Introduce B into A; add C, followed by D and then E.

EXAMPLE 9

Antisun Milk

| FORMULA | | |
|---|---|---|
| A | Sepiperl ™ N: | 3.0% |
| | Sesame oil: | 5.0% |
| | Parsol ™ MCX: | 5.0% |
| | λ-Carrageenan | 0.10% |
| B | Water: | q.s. 100% |
| C | Compound of Example 1: | 0.80% |
| D | Fragrance: | q.s. |
| | Preserving agent: | q.s. |

Procedure

Emulsify B in A at 75° C., then add C at about 60° C., followed by D at about 30° C., and adjust the pH if necessary.

EXAMPLE 10

Massage Gel

| FORMULA | | |
|---|---|---|
| A | Compound of Example 1: | 3.5% |
| | Water: | 20.0% |
| B | Dye: | 2 drops/100 g |
| | Water: | q.s. |
| C | Alcohol: | 10% |
| | Menthol: | 0.10% |
| D | Silicone oil: | 5.0% |

Procedure

Add B to A; then add C to the mixture, followed by D.

EXAMPLE 11

Massage Care Gel

| FORMULA | | |
|---|---|---|
| A | Compound of Example 1: | 3.00% |
| | Water: | 30% |
| B | Sepicide ™ CI: | 0.20% |
| | Sepicide ™ HB: | 0.30% |
| | Fragrance: | 0.05% |
| C | Dye: | q.s. |
| | Water: | q.s. 100% |
| D | Micropearl ™ SQL: | 5.0% |
| | Lanol ™ 1688: | 2% |

Procedure

Prepare A; add B, followed by C and then D.

EXAMPLE 12

Radiant-effect Gel

FORMULA

| | | |
|---|---|---|
| A | Compound of Example 1: | 4% |
|   | Water: | 30% |
| B | Elastine HPM: | 5.0% |
| C | Micropearl ™ M 100: | 3% |
|   | Water: | 5% |
| D | Sepicide ™ CI: | 0.2% |
|   | Sepicide ™ HB: | 0.3% |
|   | Fragrance: | 0.06% |
|   | 50% sodium pyrrolidinonecarboxylate: | 1% |
|   | Water: | q.s. 100% |

Procedure

Prepare A; add B, followed by C and then D.

EXAMPLE 13

Body Milk

FORMULA

| | |
|---|---|
| Montanov ™ 68: | 5% |
| Sweet almond oil: | 5% |
| Water: | q.s. 100% |
| Compound of Example 1: | 0.3% |
| Glycerol: | 5% |
| Preserving agent: | 0.2% |
| Fragrance: | 0.3% |

Procedure

Melt A at about 75° C. Emulsify B in A at 75° C. and then add C at about 60° C., followed by D.

EXAMPLE 14

Make-up-removing Emulsion Containing Sweet Almond Oil

FORMULA

| | | |
|---|---|---|
| A | Sepiperl ™ N: | 3.0% |
|   | Glyceryl triheptanoate: | 10.0% |
| B | Water: | q.s. 100% |
| C | Compound of Example 1: | 1.0% |
| D | Fragrance: | q.s. |
|   | Preserving agent: | q.s. |

EXAMPLE 15

Moisturizing Cream for Greasy Skin

FORMULA

| | | |
|---|---|---|
| A | Montanov ™ 68: | 5% |
|   | Cetylstearyl octanoate: | 8% |
|   | Octyl palmitate: | 2% |
|   | Water: | q.s. 100% |
|   | Compound of Example 1: | 0.6% |
|   | Micropearl ™ M100: | 3.0% |
|   | Mucopolysaccharides | 5% |

-continued

FORMULA

| | |
|---|---|
| Sepicide ™ HB: | 0.8% |
| Fragrance: | 0.3% |

EXAMPLE 16

Alcohol-free, Soothing After-shave Balm

FORMULA

| | |
|---|---|
| Mixture of laurylamino acids | 0.1% to 5% |
| Magnesium potassium aspartate: | 0.002% to 0.5% |
| Lanol ™ 99: | 2% |
| Sweet almond oil: | 0.5% |
| Water: | q.s. 100% |
| Compound of Example 1: | 3% |
| Sepicide ™ HB: | 0.3% |
| Sepicide ™ CI: | 0.2% |
| Fragrance: | 0.4% |

EXAMPLE 17

Cream Containing AHAs for Sensitive Skin

FORMULA

| | |
|---|---|
| Mixture of laurylamino acids: | 0.1% to 5% |
| Magnesium potassium aspartate: | 0.002% to 0.5% |
| Lanol ™ 99: | 2% |
| Montanov ™ 68: | 5.0% |
| Water: | q.s. 100% |
| Compound of Example 1: | 1.50% |
| Gluconic acid: | 1.50% |
| Triethanolamine: | 0.9% |
| Sepicide ™ HB: | 0.3% |
| Sepicide ™ CI: | 0.2% |
| Fragrance: | 0.4% |

EXAMPLE 18

Aftersun Soothing Care Product

FORMULA

| | |
|---|---|
| Mixture of lauryl amino acids: | 0.1% to 5% |
| Magnesium potassium aspartate: | 0.002% to 0.5% |
| Lanol ™ 99: | 10.0% |
| Water: | q.s. 100% |
| Compound of Example 1: | 2.50% |
| Sepicide ™ HB: | 0.3% |
| Sepicide ™ CI: | 0.2% |
| Fragrance: | 0.4% |
| Dye: | 0.03% |

EXAMPLE 19

Make-up-removing Milk

| FORMULA | |
|---|---|
| Sepiperl ™ N: | 3% |
| Primol 352: | 8.0% |
| Sweet almond oil: | 2% |
| Water: | q.s. 100% |
| Compound of Example 1: | 0.8% |
| Preserving agent: | 0.2% |

EXAMPLE 20

Body Milk

| FORMULA | |
|---|---|
| Sepiperl ™ N: | 3.5% |
| Lanol ™ 37T: | 8.0% |
| Solagum ™ L: | 0.05% |
| Water: | q.s. 100% |
| Benzophenone: | 2.0% |
| Dimethicone 350 cPs: | 0.05% |
| Compound of Example 1: | 0.8% |
| Preserving agent: | 0.2% |
| Fragrance: | 0.4% |

EXAMPLE 21

Alkaline-pH Fluid Emulsion

| | |
|---|---|
| Marcol ™ 82: | 5.0% |
| NaOH: | 10.0% |
| water: | q.s. 100% |
| Compound of Example 1: | 1.5% |

EXAMPLE 22

Fluid Foundation

| FORMULA | |
|---|---|
| Simusol ™ 165: | 5.0% |
| Lanol ™ 84D: | 8.0% |
| Lanol ™ 99: | 5.0% |
| Water: | q.s. 100% |
| Inorganic fillers and pigments: | 10.0% |
| Compound of Example 1: | 1.2% |
| Preserving agent: | 0.2% |
| Fragrance: | 0.4% |

EXAMPLE 23

Antisun Milk

| FORMULA | |
|---|---|
| Sepiperl ™ N: | 3.5% |
| Lanol ™ 37T: | 10.0% |

-continued

| FORMULA | |
|---|---|
| Parsol NOX ™: | 5.0% |
| Eusolex ™ 4360: | 2.0% |
| Water: | q.s. 100% |
| Compound of Example 1: | 1.8% |
| Preserving agent: | 0.2% |
| Fragrance: | 0.4% |

EXAMPLE 24

Eye Contour Gel

| FORMULA | |
|---|---|
| Compound of Example 1: | 2.0% |
| Fragrance: | 0.06% |
| Sodium pyrrolidinonecarboxylate: | 0.2% |
| Dow Corning ™ 245 Fluid | 2.0% |
| Water: | q.s. 100% |

EXAMPLE 25

Leave-in Care Composition

| FORMULA | |
|---|---|
| Compound of Example 1: | 1.5% |
| Fragrance: | q.s. |
| Preserving agent: | q.s. |
| Dow Corning ™ X2 8360: | 5.0% |
| Dow Corning ™ Q2 1401: | 15% |
| Water: | q.s. 100% |

EXAMPLE 26

Slimming Gel

| | |
|---|---|
| Compound of Example 1: | 5% |
| Ethanol: | 30% |
| Menthol: | 0.1% |
| Caffeine: | 2.5% |
| Extract of butcher's-broom: | 2% |
| Extract of ivy: | 2% |
| Sepicide ™ HB: | 1% |
| Water: | q.s. 100% |

EXAMPLE 27

Alcohol-free, Soothing After-shave Balm

| | FORMULA | |
|---|---|---|
| A | Lipacide ™ PVB: | 1.0% |
| | Lanol ™ 99: | 2.0% |
| | Sweet almond oil: | 0.5% |
| B | Compound of Example 1 | 3.5% |
| C | Water: | q.s. 100% |

-continued

| | FORMULA | |
|---|---|---|
| D | Fragrance: | 0.4% |
| | Sepicide ™ HB: | 0.4% |
| | Sepicide ™ CI: | 0.2% |

EXAMPLE 28

Refreshing After-shave Gel

| | FORMULA | |
|---|---|---|
| A | Lipacide ™ PVB: | 0.5% |
| | Lanol ™ 99: | 5.0% |
| | Compound of Example 1 | 2.5% |
| B | Water: | q.s. 100% |
| C | Micropearl ™ LM: | 0.5% |
| | Fragrance: | 0.2% |
| | Sepicide ™ HB: | 0.3% |
| | Sepicide ™ CI: | 0.2% |

EXAMPLE 29

Care Product for Greasy Skin

| | FORMULA | |
|---|---|---|
| A | Micropearl ™ M310: | 1.0% |
| | Compound of Example 1 | 5.0% |
| | Octyl isononanoate: | 4.0% |
| B | Water: | q.s. 100% |
| C | Sepicontrol ™ A5: | 4.0% |
| | Fragrance: | 0.1% |
| | Sepicide ™ HB: | 0.3% |
| | Sepicide ™ CI: | 0.2% |
| D | Capigel ™ 98: | 0.5% |
| | Water: | 10% |

EXAMPLE 30

Cream Containing AHAs

| | FORMULA | |
|---|---|---|
| A | Montanov ™ 68: | 5.0% |
| | Lipacide ™ PVB: | 1.05% |
| | Lanol ™ 99: | 10.0% |
| B | Water: | q.s. 100% |
| | Gluconic acid: | 1.5% |
| | TEA (triethylamine): | 0.9% |
| C | Compound of Example 1 | 1.5% |
| D | Fragrance: | 0.4% |
| | Sepicide ™ HB: | 0.2% |
| | Sepicide ™ CI: | 0.4% |

EXAMPLE 31

Non-greasy Self-tanning Product for the Face and the Body

| | FORMULA | |
|---|---|---|
| A | Lanol ™ 2681: | 3.0% |
| | Compound of Example 1 | 2.5% |
| B | Water: | q.s. 100% |
| | Dihydroxyacetone: | 3.0% |
| C | Fragrance: | 0.2% |
| | Sepicide ™ HB: | 0.8% |
| | NaOH (sodium hydroxide): | q.s. pH = 5 |

EXAMPLE 32

Antisun Milk Containing Tahitian Monoi Oil

| | FORMULA | |
|---|---|---|
| A | Tahitian monoï oil: | 10% |
| | Lipacide ™ PVB: | 0.5% |
| | Compound of Example 1 | 2.2% |
| B | Water: | q.s. 100% |
| C | Fragrance: | 0.1% |
| | Sepicide ™ HB: | 0.3% |
| | Sepicide ™ CI: | 0.1% |
| | Octyl methoxycinnamate: | 4.0% |

EXAMPLE 33

Antisun Care Product for the Face

| | FORMULA | |
|---|---|---|
| A | Cyclomethicone and dimethiconol: | 4.0% |
| | Compound of Example 1 | 3.5% |
| B | Water: | q.s. 100% |
| C | Fragrance: | 0.1% |
| | Sepicide ™ HB: | 0.3% |
| | Sepicide ™ CI: | 0.21% |
| | Octyl methoxycinnamate: | 5.0% |
| | Titanium mica: | 2.0% |
| | Lactic acid: | q.s. pH = 6.5 |

EXAMPLE 34

Self-tanning Emulsion

| | FORMULA | |
|---|---|---|
| A | Lanol ™ 99: | 15% |
| | Montanov ™ 68: | 5.0% |
| | Octyl para-methoxycinnamate: | 3.0% |
| B | Water: | q.s. 100% |
| | Dihydroxyacetone: | 5.0% |
| | Monosodium phosphate: | 0.2% |
| C | Compound of Example 1 | 0.5% |
| D | Fragrance: | 0.3% |
| | Sepicide ™ HB: | 0.8% |
| | NaOH: | q.s. pH = 5 |

EXAMPLE 35

Sheen Gel

| | |
|---|---|
| Compound of Example 1 | 1.5% |
| Volatile silicone | 25% |
| Monopropylene glycol | 25% |
| Demineralized water | 10% |
| Glycerol | q.s. 100% |

EXAMPLE 36

Slimming Gel

| | |
|---|---|
| Compound of Example 1 | 1.5% |
| Isononyl isononanoate | 2% |
| Caffeine | 5% |
| Ethanol | 40% |
| Micropearl ™ LM | 2% |
| Demineralized water | q.s. 100% |
| Preserving agent, fragrance | q.s. |

EXAMPLE 37

Make-up-removing Milk

| | |
|---|---|
| Simulsol ™ 165 | 4% |
| Montanov ™ 202 | 1% |
| Triglyceride caprylate caprate | 15% |
| Pecosil ™ DCT | 1% |
| Demineralized water | q.s. |
| Capigel ™ 98 | 0.5% |
| Compound of Example 1 | 1% |
| Proteol ™ oat | 2% |
| NaOH | q.s. pH 7 |

EXAMPLE 38

Antisun Cream

| | |
|---|---|
| Simulsol ™ 165 | 3% |
| Montanov ™ 202 | 2% |
| $C_{12}$—$C_{15}$ benzoate | 8% |
| Pecosil ™ PS 100 | 2% |
| Dimethicone | 2% |
| Cyclomethicone | 5% |
| Octyl methoxycinnamate | 6% |
| Benzophenone-3 | 4% |
| Titanium oxide | 8% |
| Xanthan gum | 0.2% |
| Butylene glycol | 5% |
| Demineralized water | q.s. 100% |
| Compound of Example 1 | 1.5% |
| Preserving agent, fragrance | q.s. |

EXAMPLE 39

Care Gel for Mixed Skin

| | |
|---|---|
| Compound of Example 1 | 4% |
| Plant squalane | 5% |
| Dimethicone | 1.5% |
| Sepicontrol ™ A5 | 4% |
| Xanthan gum | 0.3% |
| Water | q.s. 100% |
| Preserving agent, fragrance | q.s. |

EXAMPLE 40

Perfumed Body Mask

| | |
|---|---|
| Compound of Example 1 | 1.5% |
| Cyclomethicone | 5% |
| Fragrance | 2% |
| Micropearl ™ M100 | 5% |
| Glycerol | 5% |
| Demineralized water | q.s. 100% |

EXAMPLE 41

Cream with Vitamins

| | |
|---|---|
| Simulsol ™ 165 | 5% |
| Montanov ™ 202 | 1% |
| Caprylic/capric triglycerides | 20% |
| Vitamin A palmitate | 0.2% |
| Vitamin E acetate | 1% |
| Micropearl ™ M305 | 1.5% |
| Compound of Example 1 | 0.7% |
| Water | q.s. 100% |
| Preserving agent, fragrance | q.s. |

Montanov™ 68 (cetearyl glucoside) is a self-emulsifying composition as described in WO 92/06778, sold by the company SEPPIC.

Micropearl™ M100 is an ultra-fine powder with a very soft feel sensation and a matt effect, sold by the company Matsumo.

Sepicide™ CI, imidazolinurea, is a preserving agent sold by the company SEPPIC.

Pemulen™ TR is an acrylic polymer sold by Goodrich.

Simulsol™ 165 is self-emulsifying glyceryl stearate, sold by the company SEPPIC.

Lanol™ 1688 is a non-greasy emollient ester sold by the company SEPPIC.

Lanol™ 14M and Lanol® S are consistency factors sold by the company SEPPIC.

Sepicide™ HB, which is a mixture of phenoxyethanol, methylparaben, ethylparaben, propylparaben and butylparaben, is a preserving agent sold by the company SEPPIC.

Monteine™ CA is a moisturizer sold by the company SEPPIC.

Schercemol™ OP is a non-greasy emollient ester.

Lanol™ P is a stabilizing additive sold by the company SEPPIC.

Parsol™ MCX is octyl para-methoxycinnamate, sold by the company Givaudan.

Sepiperl™ N is a pearlescent agent, sold by the company SEPPIC, based on a mixture of alkylpolyglucosides such as those described in WO 95/13863.

Micropearl™ SQL is a mixture of microparticles containing squalane, which is released under the action of massaging; it is sold by the company Matsumo.

Lanol™ 99 is isononyl isononanoate, sold by the company SEPPIC.

Lanol™ 37T is glyceryl triheptanoate, sold by the company SEPPIC.

solagum™ L is a carrageenan sold by the company SEPPIC.

Marcol™ 82 is a liquid paraffin sold by the company Exxon.

Lanol™ 84D is dioctyl malate, sold by the company SEPPIC.

Parsol™ NOX is a sunscreen sold by the company Givaudan.

Eusolex™ 4360 is a sunscreen sold by the company Merck.

Dow Corning™ 245 Fluid is cyclomethicone, sold by the company Dow Corning.

Lipacide™ PVB is an acylated wheat protein hydrolysate sold by the company SEPPIC.

Micropearl™ LM is a mixture of squalane, polymethyl methacrylate and menthol, sold by the company SEPPIC.

Sepicontrol™ A5 is a mixture of capryloylglycine, sarcosine and extract of Cinnamon zylanicum, sold by the company SEPPIC, such as those described in International patent application PCT/FR 98/01313 filed on Jun. 23, 1998.

Capigel™ 98 is an acrylic copolymer sold by the company SEPPIC.

Lanol™ 2681 is a coconut caprylate/caprate mixture sold by the company SEPPIC.

Montanov™ 202 is an APG/fatty alcohol composition as described in WO 98/47610, sold by the company SEPPIC.

What is claimed is:

1. Composition consisting essentially of an oil phase, an aqueous phase, at least one water-in-oil (W/O) emulsifier, at least one oil-in water (O/W) emulsifier;

said composition being an inverted latex comprising from 20% to 70% by weight of a branched or crosslinked anionic polyelectrolyte of a monomer possessing a strongly acidic group and comprising 2-methyl-2-[(1-oxo-2-propenyl)amino]-1-propane-sulphonic acid which is partially or totally salinized in the form of the sodium salt or the ammonium salt;

said composition containing from 2.5% to 15% by weight, of emulsifiers, among which from 20% to 50% of the total weight of the emulsifiers present are water-in-oil (W/O) emulsifiers, and among which from 80% to 50% of the total weight of the emulsifiers are oil-in-water (O/W) emulsifiers, and in which the anionic polyelectrolyte is crosslinked and/or branched with diethylenic or polyethylenic compounds in a molar proportion, expressed relative to the monomers used, of from 0.005% to 1%;

said crosslinking agent and/or the branching agent being selected from the group consisting of ethylene glycol methacrylate, sodium diallyloxyacetate, diethylene glycol, diacrylate, diallylurea, trimethylopropane triacrylate and methylenebisacrylamide; and said oil phase representing from 15% to 40% of the total weight of the composition.

2. The composition according to claim 1, wherein the oily phase is made up of isohexadecane or white mineral oil.

3. The composition according to claim 1, wherein said composition also contains one or more additives selected from the group consisting of complexing agents, transfer agents and chain-limiting agents.

4. Cosmetic, dermo-pharmaceutical or pharmaceutical composition comprising from 0.1% to 10% by weight of an inverted latex as defined in claim 1.

5. The composition as defined in claim 4, in the form of a milk, a lotion, a gel, a cream, a soap, a foam bath, a balm, a shampoo or a conditioner.

6. Soothing composition for sensitive skin, comprising an inverted latex as defined in claim 1, and one or more N-acylated amino acids.

* * * * *